US006975991B2

(12) United States Patent
Basson et al.

(10) Patent No.: US 6,975,991 B2
(45) Date of Patent: Dec. 13, 2005

(54) WEARABLE DISPLAY SYSTEM WITH INDICATORS OF SPEAKERS

(75) Inventors: Sara H. Basson, White Plains, NY (US); Dimitri Kanevsky, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 740 days.

(21) Appl. No.: 09/774,925

(22) Filed: Jan. 31, 2001

(65) Prior Publication Data

US 2002/0103649 A1  Aug. 1, 2002

(51) Int. Cl.[7] .............................................. G01L 21/06
(52) U.S. Cl. ................................................... 704/271
(58) Field of Search .............................. 704/271, 270, 704/275; 348/14.08, 14, 14.09, 14.16, 15; 359/630; 381/68.1; 709/204; 395/2.4, 806

(56) References Cited

U.S. PATENT DOCUMENTS

| | | | |
|---|---|---|---|
| 5,029,216 A * | 7/1991 | Jhabvala et al. ............. 381/313 |
| 5,335,011 A * | 8/1994 | Addeo et al. ............... 348/14.1 |
| 5,473,726 A * | 12/1995 | Marshall ..................... 704/231 |
| 5,506,626 A | 4/1996 | Yagi et al. |
| 5,537,151 A | 7/1996 | Orr et al. |
| 5,657,088 A | 8/1997 | Hankinson |
| 5,734,923 A * | 3/1998 | Sagawa et al. .......... 715/500.1 |
| 5,737,431 A | 4/1998 | Brandstein et al. |
| 5,916,302 A * | 6/1999 | Dunn et al. .................. 709/204 |
| 5,940,118 A * | 8/1999 | Van Schyndel .......... 348/14.05 |
| D436,960 S | 1/2001 | Budd et al. |
| 6,222,677 B1 | 4/2001 | Budd et al. |
| 6,240,392 B1 * | 5/2001 | Butnaru et al. ............. 704/271 |
| 6,351,273 B1 * | 2/2002 | Lemelson et al. .......... 715/786 |
| 6,377,296 B1 | 4/2002 | Zlatsin et al. |
| 6,377,925 B1 * | 4/2002 | Greene et al. ............... 704/271 |
| 6,466,250 B1 * | 10/2002 | Hein et al. ................ 348/14.16 |
| 6,593,956 B1 * | 7/2003 | Potts et al. ............... 348/14.09 |

FOREIGN PATENT DOCUMENTS

WO  WO 99/23524  *  5/1999  ............ G02C 1/00

OTHER PUBLICATIONS

Michael Brandstein, "Real-Time Face Tracking Using Audio and Image Data", 1998.*
Personal Captioning System, "Live Theater Captioning System," Oct. 21, 1999.*
U.S. Appl. No. 09/774,930, filed Jan. 31, 2001, "Universal Closed Caption Portable Receiver.".

(Continued)

Primary Examiner—W. R. Young
Assistant Examiner—Jakieda R Jackson
(74) Attorney, Agent, or Firm—Ryan, Mason & Lewis, LLP

(57) ABSTRACT

Methods and systems for creating a comfortable, user-friendly environment that allows a hearing impaired user to identify who is speaking and preferably what is being said during interactions with other individuals, e.g., at any form of meeting. In accordance with the invention, it is determined whether or not someone is speaking. If yes, then the speaker's position is identified. It is also determined whether the speaker is in the range of view for the user's display. If yes, an illuminated dot is projected above the speaker on a wearable display to show the user where the speaker is located. If no, a directional arrow is projected on the display to indicate to the user which way he should look to see the current speaker.

26 Claims, 5 Drawing Sheets

OTHER PUBLICATIONS

U.S. Appl. No. 09/437,793, filed Nov. 10, 1999, "Compact Illumination System Providing Improved Field of View for Virtual Display Applications.".

U.S. Appl. No. 09/369,707, filed Aug. 6, 1999, "Methods and Apparatus for Audio-Visual Speech Detection and Recognition.".

* cited by examiner

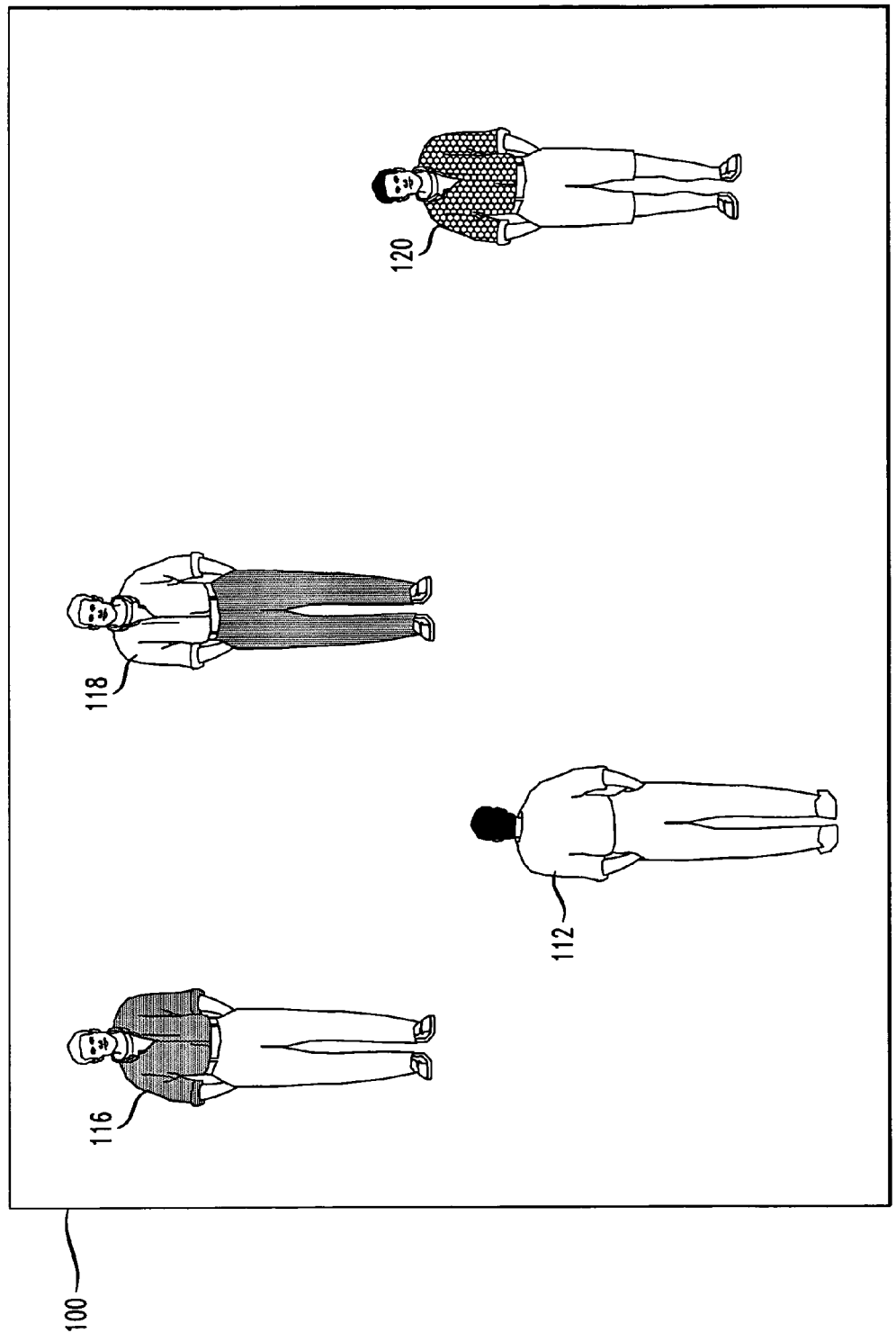

WEARABLE DISPLAY SYSTEM WITH INDICATORS OF SPEAKERS

CROSS REFERENCE TO RELATED APPLICATIONS

This application is related to the U.S. patent application Ser. No. 09/774,930, entitled "Universal Closed Caption Portable Receiver," filed Jan. 31, 2001, and the disclosure of which is incorporated by reference herein.

FIELD OF THE INVENTION

The invention is generally related to techniques for improving transcription services for the hearing impaired and, more particularly, to methods and apparatus capable of indicating speakers in accordance with a wearable display system.

BACKGROUND OF THE INVENTION

Many problems exist in today's world for a disabled individual with respect to the individual's interaction with others. The present invention focuses mainly on individuals with hearing impediments and their ability to interact with people in certain situations, e.g., at meetings. For example, when a deaf person is at a meeting he or she is unable to understand what is being said or by whom.

One unique solution designed to provide a remedy to this problem is disclosed in the U.S. patent application Ser. No. 09/774,930, entitled "Universal Closed Caption Portable Receiver," filed Jan. 31, 2001, and the disclosure of which is incorporated by reference herein. In one illustrative aspect disclosed in the U.S. patent application Ser. No. 09/774,930, a portable and universal closed caption receiving device is provided for receiving a text-based signal from a stenographic transcription service. The text corresponds to audio content associated with some live performance or activity at which the wearer of the device is present and/or participating in. The closed caption receiving device is used in conjunction with a display system carried by the user such as, for example, a wearable head mounted display. The closed captioning device receives the textual transcription from the transcription service provider while the user watches (participates in) the live event. The text is provided to the head mounted display worn by the user such that the displayed text may be read by the user at the same time the user is able to view the event through the display itself. Also disclosed, as an alternative embodiment, the text displayed to the wearer may be generated by a voice recognition system resident on (or remote from but connected to) the closed caption receiving device, rather than by a stenographic transcription service.

The U.S. patent application Ser. No. 09/774,930 discloses many examples of head mounted displays that may be employed, e.g., the eyeglass-based microdisplay system available from MicroOptical Corporation (Westwood, Mass.); the ergonomic wearable personal display from Invisio Inc. (Sunnydale, Calif.); and the compact optical display system associated with the wearable personal computer from IBM Corporation (Armonk, N.Y.) as described, for example, in U.S. patent applications identified by Ser. No. 09/437,972 filed Nov. 10, 1999; Ser. No. 09/437,793 filed on Nov. 10, 1999; and/or Ser. No. 29/110,706 filed on Sep. 10, 1999, assigned to the present assignee and incorporated by reference herein. However, it is pointed out that one of ordinary skill in the art will realize various other wearable display systems that may be employed in conjunction with the closed caption receiver.

While the solution provided by the above-described closed caption receiving system provides individuals with hearing impairments with an extremely useful solution, in certain circumstances the individual, himself, may not always be able to identify who is speaking if there are several people participating in the meeting. That is, while the user can see transcriptions of the speech that is going on in the meeting, there may be several speakers in the room, and if the user does not look at the speaker at the moment he or she started to speak, the user may miss the information about who is speaking especially if a speaker asked a short question. Also, a person may be speaking but the user may not know where that person is and may end up looking at the wrong person when they see that person's lips moving.

Further, even in the situation where a stenographic transcription or voice recognition result associates a name with the displayed text, the hearing impaired individual may not know the names of the speakers in the meeting and, thus, displaying the name of the speaker with the text would still not help the user to easily identify who is speaking.

Alternatively, it is possible to have a live aid at the site of the meeting and have the aid somehow communicate with the handicapped person, via sign language or any other form of communication, in order to indicate who is speaking and what they are saying. While this can be an efficient solution, it requires a significant amount of time for the actual translation process and some context may be lost. Also, the task of finding an available aid may be difficult. Still further, besides being time consuming, use of a live aid for an extended period of time can be very expensive.

SUMMARY OF THE INVENTION

The present invention provides methods and systems for creating a comfortable, user-friendly environment that allows a hearing impaired user to know who is currently speaking during interactions with other individuals, e.g., at any form of meeting, and preferably to know what is being said during such interactions.

In one illustrative aspect, the invention provides a visual indicator system with a wearable display system which comprises a processing device and a display coupled thereto, both preferably to be worn by an individual with a hearing impediment. The wearable display system indicates to the user, in accordance with one or more visual indicators presented on the display, who is currently speaking in a conversation or meeting in which the user is engaged. An indication of who is speaking allows the user to be able to accurately turn his attention to that person so that, absent a textual transcription (which may, however, also be provided), the user may begin reading the speakers lip movements. That is, it is extremely useful for a hearing impaired user who is capable of lip reading to have a visual indication of who is currently speaking so that he or she will be looking in the correct direction when the speaker is speaking. In one embodiment, the indication comprises projecting a marker, e.g., an illuminated circle or dot, on the display over the head of the individual that is currently speaking.

Further, during the situation when the person currently speaking is not in the field or area of view of the user, the wearable display system also provides an indication on the display to the user as to what direction to look to see the person currently speaking in the meeting. In one embodiment, the indication comprises projecting a marker on the display, e.g., an arrow, in the direction of the individual that is currently speaking. The user may then turn to that person and begin lip reading. It is to be appreciated that the field of view of the user can be defined differently depending on the type of a wearable display employed by the system. The field of view can be defined as the area that represents the viewable area of the wearable display. Alternatively, the field of view can be defined as the area that is viewed by the user's eyes at any one moment.

It is to be appreciated that the present invention may employ one or more methods of identifying the location of the current speaker and determining where on the display to present the one or more visual indicators. In a video-based approach, this may comprise using one or more cameras to track the meeting participants and one or more cameras to provide an indication as to what the field of view of the user currently is. Based on this data, a determination as to where to place the visual indicators may be made. It is to be appreciated that an audio-based approach may alternatively be employed. By way of one example, the current speaker may be located through detection of sound wave phase as a function of frequencies using two or more microphones. Of course, it is to be understood that the invention is not limited to a particular method of identifying the location of the current speaker.

Furthermore, as mentioned, the wearable display system preferably receives and/or generates a transcription of audio content associated with an event that the user is attending and/or participating in. The audio content transcription is presented to the user in accordance with the display. For instance, in the case where the user is participating in a meeting with one or more other participants, the textual transcription represents the speech uttered by a meeting participant speaking at given time. Thus, in accordance with the visual indicators generated and displayed by the wearable display system, the user is able to accurately attribute the audio content represented by the textual transcription to the correct speaker. All of this information is conveniently presented to the user on the display of the wearable display system.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 1A is a diagram illustrating a meeting area with multiple participants including a user of a wearable display system according to the present invention;

DETAILED DESCRIPTION OF PREFERRED EMBODIMENTS

Figure 1B:
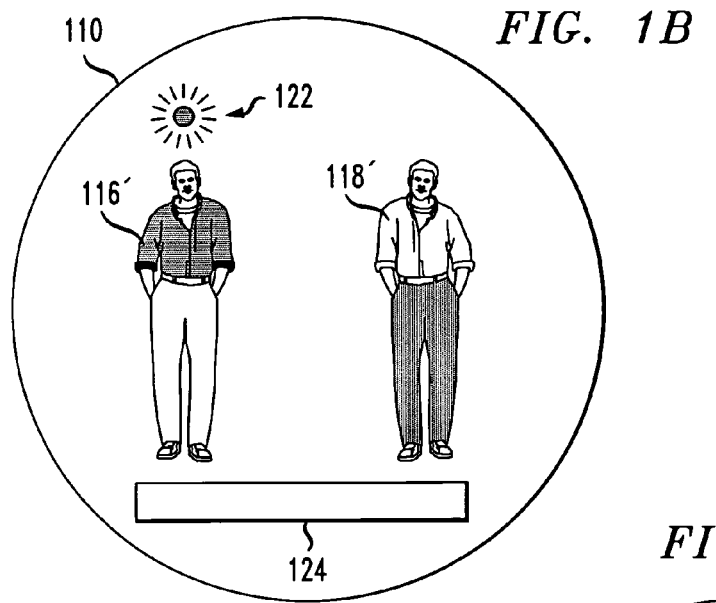
FIGS. 1B, 1C and 1D are diagrams of three respective views illustrating what a user of a wearable display system according to the present invention may see in a display associated with the system during the course of a conversation with the meeting participants of FIG. 1A.

The present invention will be described below in the context of an exemplary meeting environment with multiple participants where visual indicators and textual transcriptions of what is being said may be provided to a user of a wearable display system according to the invention. However, it is to be understood that the invention is not limited to use in any particular environment, but is rather more generally applicable for use in accordance with any environment where multiple participants engage in some form of speech in which it is desirable to be able to provide a user of a wearable display system with visual indicators of who is currently speaking.

It is to be appreciated that the remainder of the detailed description will be organized as follows. The use of visual indicators generated and displayed according to the present invention will be generally described in the context of FIGS. 1A through 1D. Then, a detailed description of various illustrative embodiments of a visual indicator system, including a wearable display system, according to the invention for generating and displaying such visual indicators will be provided in the context of FIGS. 2-4.

Specifically, FIG. 1A depicts a meeting with multiple participants, including the user of the wearable display system. As shown, three people 116, 118 and 120 are participating in the meeting, in addition to the user 112 of the wearable display system. The meeting is being held in an area 100, e.g., a conference room. It is assumed that the user 112 is a person with a hearing impediment. In terms of perspective, as shown in FIG. 1A, it is to be understood that meeting participants 116 and 118 are directly in front of user 112, while participant 120 is to the right of user 112.

Figure 1C:
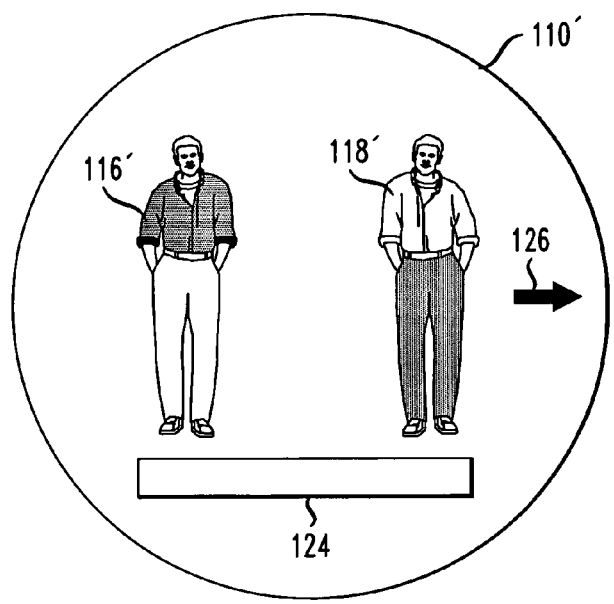
Figure 1D:
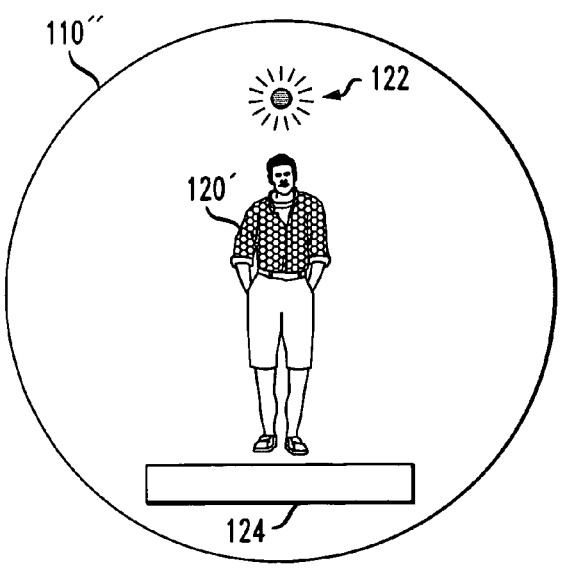

Turning now to FIG. 1B, 1C and 1D, three respective views are shown of what a user 112 of a wearable display system according to the invention may see in a display associated with the system during the course of a conversation with the meeting participants. How these views are generated will be explained in detail in the context of FIGS. 2-4. Views 110, 110' and 110" (of FIGS. 1B, 1C and 1D, respectively) are illustrated and described first in order to facilitate a generally understanding of the advantages that the wearable display system of the invention provides to a user.

In accordance with FIG. 1B, it is assumed that the user 112 wearing the wearable display is able to see meeting participants 116 and 118. That is, these two individuals are in the user's current area or field of view, as compared to participant 120 who is not in the user's current field of view. Thus, as generally depicted in FIG. 1B, participants 116 and 118 are represented as 116' and 118' in the view 110 of the system display.

How the participants are represented in accordance with the system display depends on what type of display is employed. For instance, in an eyeglasses-based microdisplay system (as will be further described below), the representations 116' and 118' of participants 116 and 118, respectively, are the actual persons themselves as the user sees them through the conventionally-transparent glass of the eyeglasses. It will be assumed that this type of display will be employed when explaining below the generation and presentation of visual indicators for use in identifying the location of the current speaker according to the invention.

However, in accordance with alternative types of displays that may be used as the wearable display to present the user with view 110, the representations 116' and 118' may take other forms. For example, the representations may be a live video image of the participants 116 and 118, whereby the video image is displayed directly on the screen of the display. In this case, while the user may see the individuals, he is also able to see a live video image of them on the display itself. Still further, the representations 116' and 118' may be a computer-generated diagrammatic graphic representation of the participants 116 and 118, whereby the computer-generated diagrammatic graphic representation is displayed directly on the screen of the display. Again, in this case, while the user may see the individuals, he is also able to see a graphic representation of them on the display itself. Of course, depending on the type of display employed, the generation and presentation of the visual indicators and the textual transcription according to the invention may differ. However, given the inventive teachings provided herein, one of ordinary skill in the art will realize various other types of displays and corresponding implementation techniques for generating and presenting such visual indicators and text.

Once the current speaker is located (as will be explained later), the wearable display system of the invention generates one or more visual indicators that inform the user which one of the meeting participants 116, 118 or 120 is currently speaking.

As shown in the view of FIG. 1B, the wearable display system generates a visual indicator 122, in the form of an illuminated circle or dot, that is displayed above the head of the representation of the participant identified as the current speaker. Of course, any type or shape of visual marker (e.g., words, symbols, etc.) can be used. Also, again depending on the display type, the representation of the participant can be visually changed in some way so as to distinguish him as the current speaker, e.g., change color of the representation of the current speaker, alter brightness of the representation of the current speaker, etc. Thus, as shown in FIG. 1B, the system has identified participant 116 as the current speaker and therefore places a marker 122 over representation 116'. Advantageously, the user can quickly visually determine who is speaking from the visual marker over the head of the individual that the system identifies as the current speaker.

Now, turning to FIG. 1C, assume that participant 116 has stopped speaking and that participant 120 has now started speaking. Since participant 120 is not currently in the field of view of the user, as shown in the view 110' of the system display in FIG. 1C, the wearable display system removes the visual indicator 122 from above representation 116' and generates a visual indicator 126, in the form of an arrow, that points the user in the direction of the current speaker. In this case, the arrow 126 directs the user to look to his right so that participant 120 is in the field of view of the system display and thus the user. Of course, it is to be understood that any directional indicator (e.g., words, symbols, etc.) may be employed to point the user in the appropriate direction (e.g., left, right, up, down, etc.).

Now, turning to FIG. 1D, assume that the user has turned his head toward his right such that participant 120 is now within the view of the user. Thus, a representation 120' of participant 120 is seen in view 110" in accordance with the system display. Since the system identified participant 120 as the current speaker, the visual indicator 122 indicating him as the current speaker is projected over his head, as shown in FIG. 1D.

It is to be understood that the wearable display system continues to update the user with these visual cues presented on the system display so that he is notified of who is currently speaking at the meeting.

While such visual cues alone serve to assist a user with a hearing disability to identify the current speaker so that the user could read the current speaker's lips, in a preferred embodiment, the wearable display system also provides the user with a textual transcription of what is being said by the current speaker. The textual transcription is represented in the respective views of FIGS. 1B, 1C and 1D as visual indication area 124. That is, the text of what each meeting participant is saying is displayed to the user 112 in area 124. This may be accomplished in a variety of ways, as will be explained later.

Now that a general illustrative understanding of the visual indicators that a wearable display system may provide to a user has been provided, the remainder of the detailed description will provide an explanation of illustrative embodiments of a system for providing a user with such visual cues to indicate who is currently speaking and, preferably, what the current speaker is saying.

Figure 2:
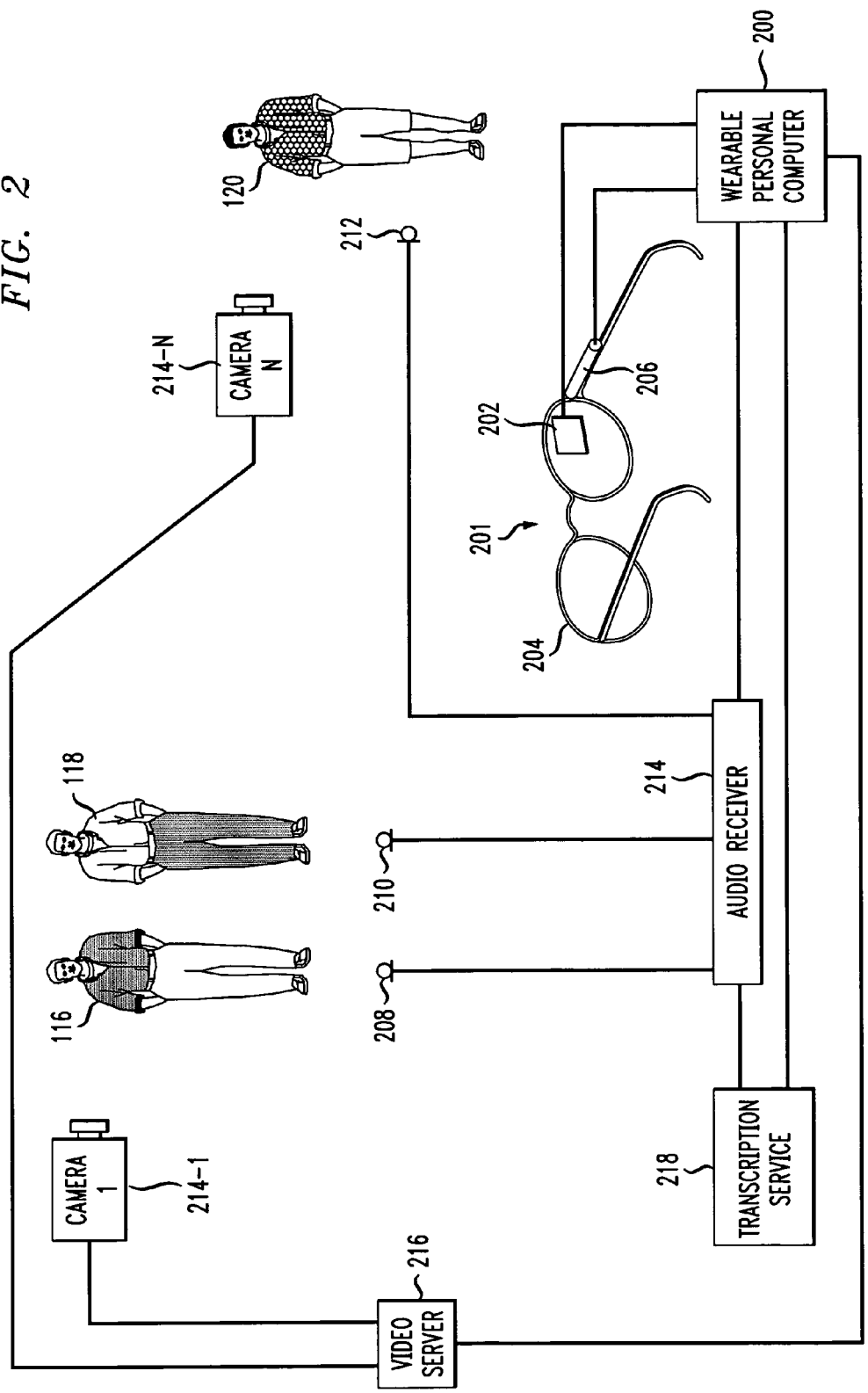
FIG. 2 is a block diagrams illustrating a first embodiment of a visual indicator system according to the present invention.

Referring now to FIG. 2, a block diagram illustrating a first embodiment of a visual indicator system according to the invention is provided. It is to be appreciated that, in the context of the meeting depicted in FIG. 1A, the visual indicator system is deployed in the meeting area 100 so as to provide the user 112 with visual cues to indicate who among participants 116, 118 and 120 is currently speaking and, preferably, what the current speaker is saying.

As shown, the visual indicator system of FIG. 2 comprises a wearable display system which, itself, comprises a wearable personal computer 200 and a wearable display 201 coupled thereto. The visual indicator system also comprises an audio receiver 214, a video server 216 and a transcription service 218. The visual indicator system also comprises microphones 208, 210 and 212 coupled to the audio receiver 214, as well as a plurality of video cameras 214-1 through 214-N, where N may equal 2, 3, 4, . . . I, coupled to the video server 216. The microphones 208, 210 and 212 are positioned in proximity to the meeting participants 116, 118 and 120, respectively. The cameras 214-1 through 214-N are positioned throughout the meeting area 100 so as to capture images of the meeting participants. It is to be understood that any of the components shown in FIG. 2, as well as the other embodiments to follow, may be coupled via a hardwired connection or a wireless connection. Also, it is to be appreciated that the audio receiver, microphones, and transcription service would not be necessary in an embodiment where no textual transcription of what the current speaker is saying is being provided.

Still further, it is to be appreciated that the wearable computer 200 may be coupled to other components of the visual indicator system, e.g., video server, audio receiver, transcription service via a local area network (LAN). Also, the audio receiver and transcription service may be connected via a LAN. Also, the transcription service may be coupled to the visual indicator system via a wide area network such as the Internet.

Further, as illustrated, the wearable display 201 comprises a microdisplay 202 and mounted on a pair of eyeglasses 204. Also, mounted on the eyeglasses 204 is a user field of view (FOV) determination device 206. In this particular embodiment, the device 206 is a miniature video camera (mini-cam) for capturing an image of what the user is actually seeing through his wearable display 201. While a user is not expressly shown, it is to be understood that the user wears the eyeglasses 204 on his or her face in a normal manner and also preferably carries the wearable personal computer 200 on his or her body, e.g., attaches the personal computer to a waist belt.

It is to be appreciated that the invention is not limited to use with any particular head mounted display system but is more generally applicable for use with any separate display system that may be carried by the user. For instance, an eyeglass-based microdisplay system such as is generally depicted in the figures is available from MicroOptical Corporation (Westwood, Mass.). Of course, it is to be understood that the MicroOptical display may be easily adapted to carry the user FOV determination device 206, in accordance with the invention, as shown in FIG. 2. However, a wide variety of other head mounted display systems may be used, e.g., the ergonomic wearable personal display from Invisio Inc. (Sunnydale, Calif.); and the compact optical display system associated with the wearable personal computer from IBM Corporation (Armonk, N.Y.) as described, for example, in U.S. patent applications identified by Ser. No. 09/437,972 filed Nov. 10, 1999; Ser. No. 09/437,793 filed on Nov. 10, 1999; and/or Ser. No. 29/110,706 filed on Sep. 10, 1999, assigned to the present assignee and incorporated by reference herein. It is to be understood that the microdisplay system may employ a microprojector for projecting the textual transcriptions and visual indicators of the invention onto the lens of the user's eyeglasses, or the text and visual indicators may be displayed on a screen associated with the microdisplay system. Given the teachings herein, one of ordinary skill in the art will realize various other wearable display systems that may be employed in conjunction with the wearable personal computer of the present invention.

Thus, how the system shown in FIG. 2 generates the visual indicators 122, 126 and the textual transcription 124, as shown in the views depicted in FIGS. 1B–1D, will now be explained.

The plurality of cameras 214-1 though 214-N are deployed throughout the meeting area so as to continually capture images of each meeting participant's location in the meeting area, as well as each meeting participant's face. The captured images are provided to the video server 216. The camera images are used by the server to determine who is the current speaker among the meeting participants. As is well-known in the art, the video server may employ techniques for extracting facial features from the images, analyzing the extracted facial features, and making a determination as to which participant's facial features are indicative of speech. For example, since lip movement is generally indicative of speech, each participant's lip region may be monitored by the cameras such that the video server 216 can make a determination as to who is currently speaking among participants 116, 118 and 120. By way of one example, the facial feature extraction and speech detection techniques disclosed in the U.S. patent application identified as Ser. No. 09/369,707, filed on Aug. 6, 1999 and entitled "Methods and Apparatus for Audio-visual Speech Detection and Recognition," the disclosure of which is incorporated by reference herein, may be employed. As indicated therein, speech recognition techniques may also be used to make the determination process more robust. Of course, other known methods may be used.

Once the video server 216 determines which one of the participants is speaking (e.g., based on visually detected lip movement), the video server can then determine the current speaker's position or location within the meeting area. The video server may do this through prestored knowledge of the dimensions of the meeting area. The location of the current speaker is needed because the visual indicator system is interested in placing a visual indicator 122 over the head of the current speaker, as the current speaker is viewed by user 112 through his wearable display 201. However, while the video server 216 can easily locate the speaker within the meeting area using cameras 214-1 through 214-N, there needs to be a correlation between the images captured by these cameras and the field of view that the user sees through his wearable display 201. That is, once the system determines the location of the current speaker, the wearable display must be instructed where to place the indicator 122 so that it is above the head of the representation of the current speaker, as shown in FIGS. 1B and 1D.

This is accomplished by the use of the mini-cam 206 mounted on the eyeglass frame 204 of the wearable display 201. As mentioned, in the case where the wearable display 201 employs a projection type microdisplay, such as the MicroOptical display system, the representations 116', 118' and 120' of participants 116, 118 and 120, respectively, are the actual persons themselves as the user sees them through the conventionally-transparent glass of the eyeglasses. Thus, by mounting a miniature video camera on the frame, the wearable personal computer 200 is provided with continually captured images representing the user's field of view (FOV).

The wearable personal computer 200 thus receives this video data, as well as the video data representing the location of the current speaker as determined by the video server 216. Then, using a predetermined image correspondence mapping, the wearable personal computer 200 determines where the visual indicator 122 is to be placed on the wearable display 201. Such a predetermined mapping may take on a variety of forms. One example may be that the mapping is a one-to-one correspondence that is determined between the location of the current speaker (as provided by the video server 216) and the video data representing what the user is currently looking at through the display 201 (as provided by the mini-cam 206). Thus, image points representing where the current speaker is located are in one-to-one correspondence to display points on the wearable display. This allows the wearable computer 200 to then generate a display signal which causes the visual indicator 122 (e.g., illuminated dot) to be projected onto the eyeglasses of wearable display 201 above the head of the current speaker, e.g., see FIG. 1B.

Likewise, if the wearable computer 200 determines that the person identified by the video server 216 as the current speaker is not currently in the view of the user (as is evident from the video data received from the mini-cam 206), then the wearable computer 200 generates a display signal which causes the visual indicator 126 (e.g., arrow) to be projected onto the eyeglasses of wearable display 201 pointing out the direction that the user should turn to in order to see the current speaker, e.g., see FIG. 1C.

Once the user turns his head in the direction of the current speaker and the current speaker is in the view of the user (again, as is evident from the video data received from the mini-cam 206), then the wearable computer 200 generates a display signal which causes the visual indicator 122 (e.g., illuminated dot) to be projected onto the eyeglasses of wearable display 201 above the head of the current speaker, e.g., see FIG. 1D.

While the visual indicator system in FIG. 2 employs a video server 216 located remote from the wearable personal computer 200, it is to be appreciated that the functions of the video server may be implemented on the wearable computer 200 itself. In an illustrative embodiment of a wearable personal computer that will be described below in the context of FIG. 4, such functionality is in fact implemented on the wearable computer 200. In such a case, the video cameras 214-1 through 214-N are coupled directly to the wearable computer 200.

It is to be understood that while such visual cues alone serve to assist a user with a hearing disability to identify the current speaker so that the user could read the current speaker's lips, in a preferred embodiment, the wearable display system also provides the user with a textual transcription of what is being said by the current speaker. This may be accomplished in a variety of ways, as will now be explained.

Referring again to FIG. 2, a transcription service 218 is coupled to the wearable personal computer 200 and to the audio receiver 214. The transcription center receives audio signals from the audio receiver 214 which represents the sounds captured by the microphones 208, 210 and 212. It is to be appreciated that, in this particular embodiment, the audio receiver 214 serves to receive the audio captured by each microphone and provide the audio data to the transcription service 218. It is to be understood that there does not have to be a direct one-to-one correspondence between the number of microphones and the number of meeting participants.

The transcription service 218, itself, may comprise: a human stenographer who transcribes the audio content, in real-time, into text; a voice recognition system which automatically recognizes the audio content, also in real-time, and outputs a textual representation of the decoded speech; or some combination of both human stenographer and automatic recognition. A text-based signal representing the transcription of the audio content is then transmitted by the transcription service 218 to the wearable personal computer 200. The computer receives the signal, extracts the textual transcription and provides it to the wearable display 201. The text is then projected on the display in area 124, in the same manner as the visual indicators are displayed, such that the user can read what the current speaker (identified by the visual indicator 122) is saying.

It is to be appreciated that the wearable personal computer 200 may include therein a closed caption receiving device as mentioned above as being disclosed in the U.S. patent application Ser. No. 09/774,930, entitled "Universal Closed Caption Portable Receiver," filed Jan. 31, 20001, and the disclosure of which is incorporated by reference herein, so that the area 124 may present transcriptions received and extracted in accordance with such a receiving device.

Thus, the user is able to receive transcriptions of the audio content of the meeting in conjunction with the enhancement of having visual cues, generated and presented in accordance with the present invention.

Alternatively, the complete transcription generation function may be implemented within the computer 200. In such case, the computer 200 may execute a speech recognition engine, resident therein, to generate the textual transcription from the audio captured by the microphones and provided directly to the computer 200 (or via the audio receiver 214). Still further, each of the meeting participants may have a computer-based laptop transcriptor which translates their audio into text directly and the text is sent to the wearable personal computer 200 for subsequent display.

Also, it is to be appreciated that while the present invention is described in the context of providing visual indicators and text to a user in association with individuals participating in a live event, the teachings of the invention are also applicable to a non-live event. For example, the visual indicator system of the invention may be used by a hearing impaired person in association with watching a movie in a movie theater. In such case, the participants (e.g., 116, 118 and 120) would not be live but rather images on the movie screen. Thus, the same operations would take place with the exception being that the video cameras capture the participants on the movie screen instead of them being live. Of course, the textual transcription could also be generated in the same way from the audio content of the movie.

Figure 3:
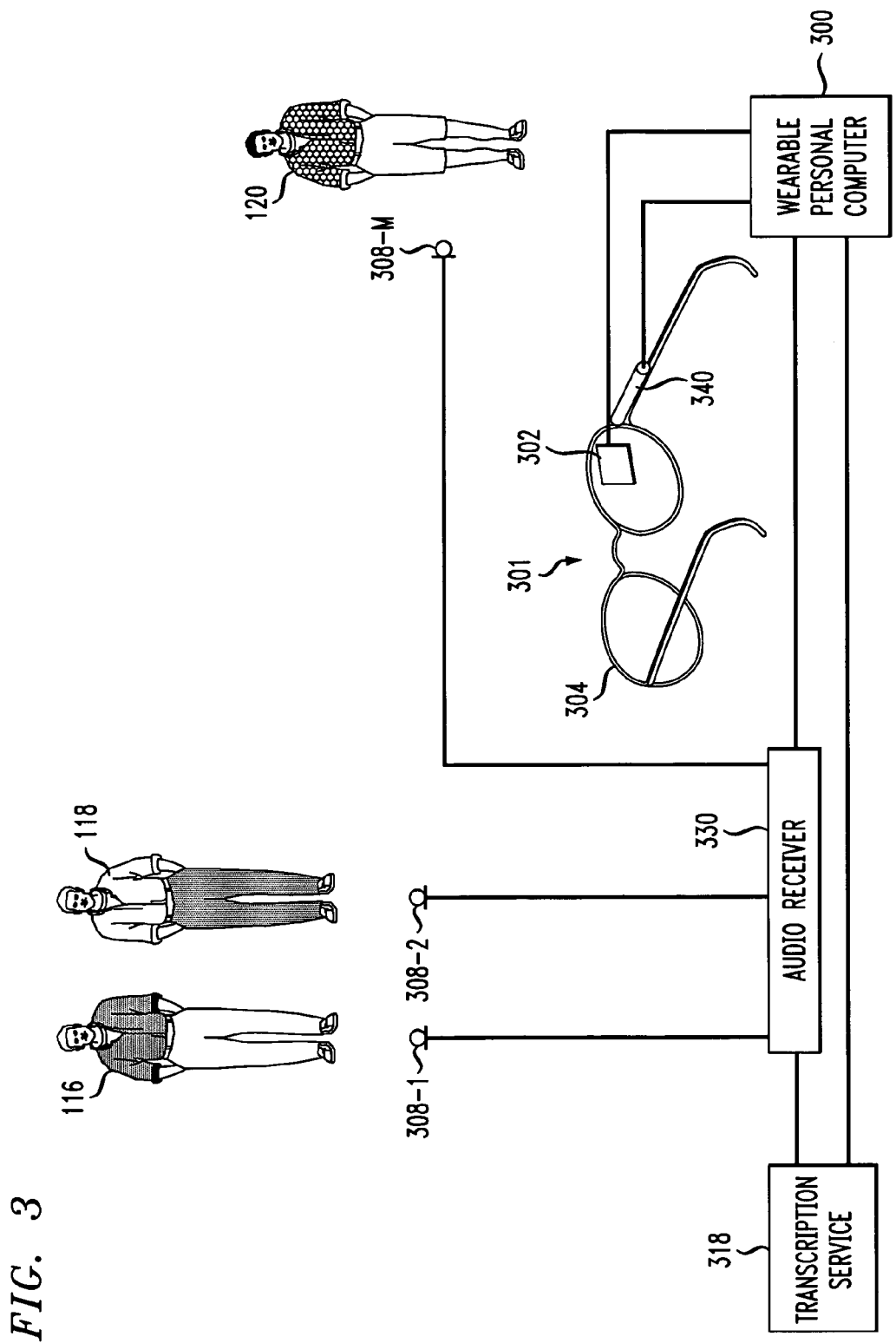
FIG. 3 is a block diagrams illustrating a second embodiment of a visual indicator system according to the present invention.

Referring now to FIG. 3, a block diagram illustrates a second embodiment of a visual indicator system according to the present invention. Specifically, FIG. 3 shows a similar wearable display system as in FIG. 2, but illustrates alternative method of identifying the location of the current speaker. Specifically, while the embodiment of FIG. 2 may be considered a video-based method of determining the location of the current speaker, the embodiment of FIG. 3 may be considered an audio-based method of doing the same.

As shown, the visual indicator system of FIG. 3 comprises a wearable personal computer 300, a wearable display 301 (including microdisplay 302 and eyeglasses 304), a transcription service 318, an audio receiver 330, and an array of microphones 308-1 through 308-M, where M may be equal to 3, 4, 5, . . . i. The wearable computer 300 and wearable display 201 may be similar to the wearable computer 200 and wearable display 201 of FIG. 2, with the following notable exceptions.

Rather than utilizing video data to make a determination of who among the meeting participants is the current speaker, the system in FIG. 3 uses audio data. This is accomplished by employing the audio receiver 330 with the array of microphones and a user field of view (FOV) determination device 340 mounted on the eyeglass frame 304. While in the embodiment of FIG. 2, the FOV determination device is implemented as a miniature video camera (mini-cam) for capturing an image of what the user is actually seeing through his wearable display 201, the device 340 in the embodiment of FIG. 3 comprises a gyroscopic/motion sensing arrangement. How these components are used to locate the current speaker and determine where on the display to project the visual indicators will now be explained.

In accordance with the array of microphones 308-1 through 308-M, the audio receiver system 330 determines the location or position of the meeting participant (116, 118 or 120) who is currently speaking. There are many ways to make this determination and the present invention is not intended to be limited to any one particular implementation.

In one embodiment, the audio receiver 330 inputs sound captured by the microphones and employs a technique for detecting sound wave phase as a function of frequencies to determine the location of the current speaker. This technique uses two or more microphones to detect the localization of a sound source, i.e., in this case, a speaker. One example of a system that may be used to perform this technique is described in U.S. Pat. No. 5,737,431 issued to Brandstein et al. on Apr. 7, 1998, the disclosure of which is incorporated by reference herein. In the Brandstein system, an array of microphones (or other sensors) is used to detect sounds (or other transmitted energy waves) emitted by objects. An advantage of using an array, as opposed to a single such sensor, is that its output can be electronically processed to emphasize sounds from a particular location and to de-emphasize sounds from other locations. One form of electronic processing that may be used here is beamforming, which makes it possible to electronically "steer" an array by emphasizing sounds from objects as they move from location to location. For these reasons, a microphone array can be advantageously used to pick up speech in situations such as teleconferences, where hands-free speech acquisition is desired, where there are multiple talkers or where there the talkers are moving. Through the use of beamforming and other such techniques, the array's directivity pattern can be updated rapidly to follow a moving talker or to switch between several alternating or simultaneous talkers. Thus, in using the Brandstein technique in accordance with the microphones 308-1 through 308-M, the audio receiver 330 is able to determine the current speaker's location.

In another embodiment, the audio receiver 330 in association with the microphones may locate the current speaker through measurement and comparison of the volume level of each person's voice. The person with the loudest voice generally tends to be the one speaking. Thus, the audio receiver system inputs the sounds captured by the microphones and compares the amplitudes of the received signals. The location from where the signal with the largest amplitude is received is assumed to be the location of the current speaker. The user may also be able to comprehend who is speaking by using visual contact and seeing who the majority of a group is looking, which generally tends to indicate who is currently speaking.

Given the location in the meeting area of the current speaker as determined by the audio receiver 330, the wearable computer 300 must correlate this to what the user is viewing through his display. In the video-based approach of FIG. 2, this was done using a mini-cam. In the audio-based approach of FIG. 3, this is done using the gyroscopic/motion sensing arrangement generally represented as element 340 in the wearable display 301. More specifically, the wearable display is fitted with a small gyroscope that is capable of giving an adequate spatial representation of where the glasses are directed, together with one or more motion sensors that provide information with regard to where the user, himself, is located in the meeting area. The information representing where the user is located and how his glasses are directed mathematically describes the field of view of the user. This data is provided to the wearable computer 300. With this data, along with the location of the current speaker as determined by the audio receiver 330, the wearable computer 300 may correlate (again, using a predetermined mapping) how each point in the field of the view matches spatial points in a room where the user is located. The wearable computer 300 then may make the determination as to where to locate the visual indicators.

It is to be appreciated that the transcription service 318 functions the same as described above in generating the textual transcription to be projected on the user's wearable display. Also, while the audio receiver 330 and the transcription service 318 are shown remote from the wearable computer 300, there respective functionalities may be implemented in the wearable computer 300.

It is to be understood that various combinations of the current speaker location techniques described in the context of FIGS. 2 and 3 may be employed. Also, depending on the type of display used for the wearable display, the system may employ other more or less complex techniques.

Figure 4:
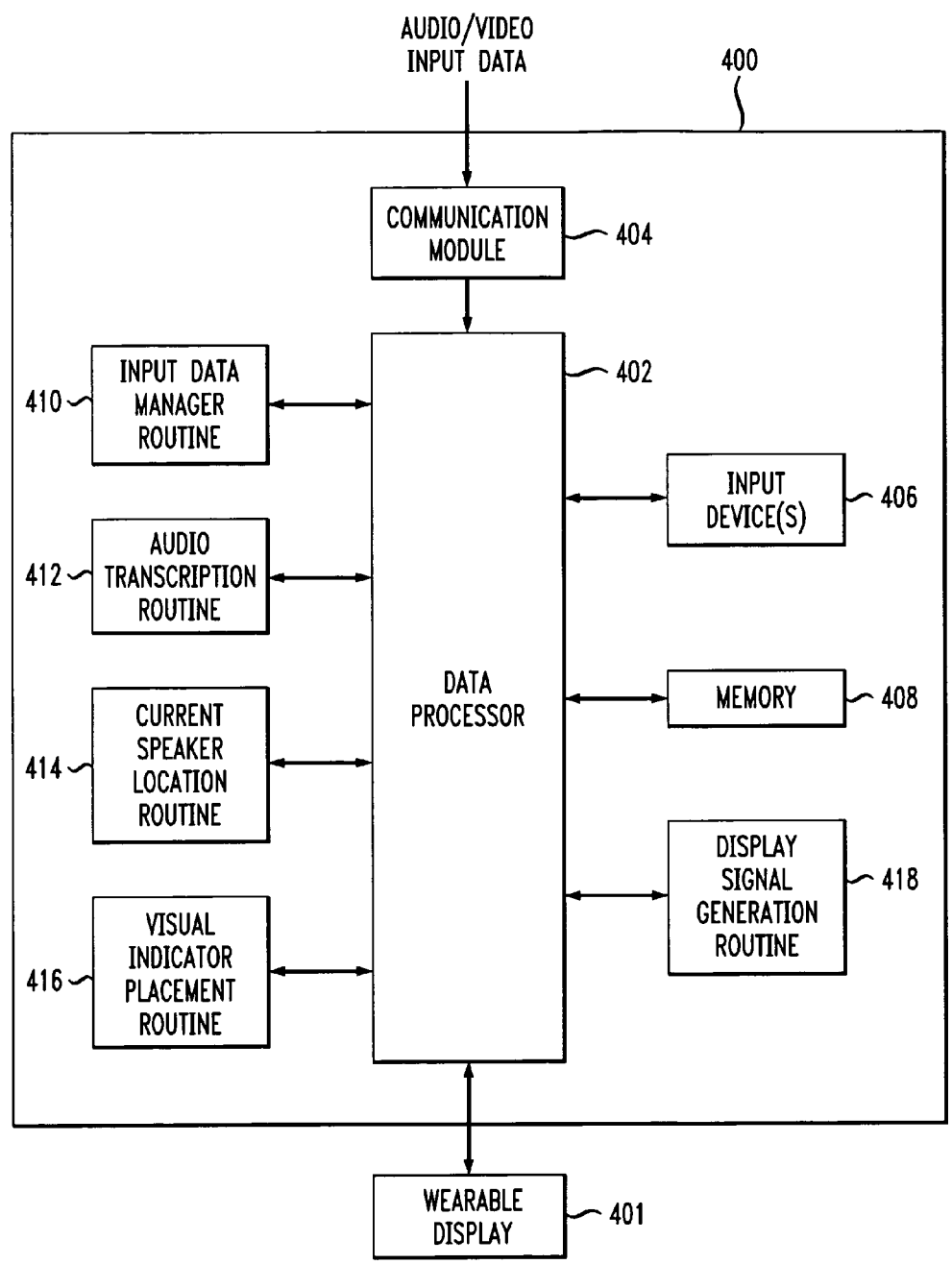
FIG. 4 is a block diagram illustrating a wearable personal computer associated with a wearable display system according to one embodiment of the present invention.

Referring now to FIG. 4, a block diagram illustrates a wearable personal computer associated with a wearable display system according to one embodiment of the present invention. It is assumed that in the particular embodiment of the wearable personal computer 400 depicted in FIG. 4, the complete transcription generation function (e.g., as performed by transcription service 218 in FIG. 2 and 318 in FIG. 3) and the current speaker location identification function (e.g., as performed by video server 216 in FIG. 2 and audio receiver 330 in FIG. 3) are implemented on the computer. Thus, wearable computer 400 may be used in the embodiments of FIGS. 2 and 3 to replace computers 200 and 300, respectively, as well as the components which perform the transcription and current speaker location functions. Wearable display 401 of FIG. 4 may be implemented as wearable display 201 of FIG. 2 or wearable display 301 of FIG. 3.

Thus, as shown in FIG. 4, the wearable personal computer 400 comprises: a data processor 402; a communication module 404 coupled to the processor 402; one or more input devices (keyboard/pen tablet) 406 coupled to the processor 402; memory 408 coupled to the processor 402; and an input data manager routine 410, an audio transcription routine 412, a current speaker location routine 414, a visual indicator placement routine 416, and a display signal generation routine 418, each of which may be loaded and executed by the processor 402 to perform its respective functions when necessary. The routines may be realized as computer software code or instructions written to cause the computer to perform the operations associated therewith. The processor 402 is also coupled to the wearable display 401.

The communication module 404 receives input data provided to the wearable personal computer from all sources, e.g., audio data from microphones (208, 210 and 212 in FIG. 2, 308-1 through 308-M in FIG. 3) and video data from cameras 214-1 through 214-N. The communication module 404 may provide for hardwired and/or wireless communication with any of the components with which it communicates. It may also include a LAN interface. The communication module 404 generally represents the communication interface for the wearable personal computer and its specific functionality depends on the communication protocol(s) employed by the wearable personal computer. It is to be understood that audio and video data interface functions are well-known in the art and thus are not described in further detail herein.

Upon receipt of data by the communication module 404, the input data manager routine 410 is loaded and executed by the processor 402 to determine what type of data it has received and what should be done with the received data. Based on this determination, another appropriate routine is loaded and executed by the processor. Memory 408 represents memory capacity used by the processor to store and execute the various routines.

For instance, when audio data is received by the communication module 404, the processor executes the audio transcription routine 412, which may be a speech recognition routine, to generate a textual transcription of what is being uttered during the meeting. This is the audio captured from the meeting participants 116, 118 and 120. The routine could also call for sending the audio data out to a remote transcription service for processing.

Further, in a video-based embodiment such as in FIG. 2, when the communication module 404 receives video data from the video cameras 214-1 through 241-N (FIG. 2), the processor 402 executes the current speaker location routine 414. This routine, as explained above, determines who is currently speaking and where that person is located in regard to the meeting area. As mentioned, this may be done using well-known facial feature extraction techniques and knowledge of the dimensions of the meeting area.

In addition, again in a video-based embodiment such as in FIG. 2, when the processor 402 receives video data from the mini-cam 206 (FIG. 2), it executes the visual indicator placement routine 416. The routine 416 uses the video data from the mini-cam and the data from the current speaker location routine 414 to determine where to generate the visual indicator to be projected on the wearable display 401 (e.g., visual indicators 122, 126). This is where the predetermined mapping, mentioned above, is employed.

It is to be appreciated that routines 414 and 416 may employ techniques for identifying and tracking moving objects and contours of moving objects as are disclosed in the U.S. patent application identified as Ser. No. 09/238,845, filed Jan. 28, 1999 and entitled "A Virtual Map System and Method for Tracking Objects," the disclosure of which is incorporated by reference herein.

Of course, in an audio-based embodiment such as in FIG. 3, routine 414 uses audio data and routine 416 uses data received from the gyroscopic/motion sensing units 340 on the wearable display to make their determinations.

The processor 402, using the display signal generation routine 418, then generates appropriate display signals for the textual transcription 124 and the visual indicators 122 and 126 to be displayed in the appropriate locations (as determined by routine 416) of the viewable area of the wearable display, e.g., see FIGS. 1B–1D. The processor 402 provides these display signals to the wearable display 401, which displays them accordingly.

Thus, in an illustrative scenario, the processor 402 does the following in accordance with the various routines. The processor determines whether or not someone is speaking. If yes, then the speaker's position is identified. It is also determined whether the speaker is in the range of view for the user's display. If yes, an illuminated dot is projected above the speaker on the wearable display to show the user where the speaker is located. If no, a directional arrow is projected on the display to indicate to the user which way he should look to see the current speaker.

The processor 402 is also connected to one or more input devices 406 such as a keyboard and/or pen tablet. Such input devices permit the user of the wearable display system to enter commands and/or other data to the wearable computer much like any other conventional computer. Depending on the command or text, the processor 402 performs the appropriate function.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method of providing a user with one or more visual indications, in accordance with a display system associated with the user, of who is currently speaking during an event in which the user is engaged, the event including one or more other individuals, the method comprising the steps of:
    identifying the location of the individual who is currently speaking during the event;
    determining whether the individual identified as the current speaker is within a field of view of the user;
    displaying a first visual indicator to the user, in accordance with the display system, in association with the individual identified as the current speaker when the individual is within the field of view of the user; and
    displaying a second visual indicator to the user, in accordance with the display system, when the individual identified as the current speaker is not within the field of view of the user, wherein the second visual indicator comprises a directional symbol displayed on the display system indicating to the user the direction to turn such that the current speaker is in the user's field of view.

2. The method of claim 1, wherein the display system is worn by the user.

3. The method of claim 1, wherein the step of identifying the location of the individual who is currently speaking during the event further comprises:
    capturing one or more video images of the one or more individuals participating in the event;
    analyzing the one or more captured video images to determine which individual has one or more facial features indicative of speech;
    designating the individual with the one or more facial features indicative of speech as the current speaker; and
    determining the location of the individual designated as the current speaker.

4. The method of claim 3, wherein the step of determining whether the individual identified as the current speaker is within the field of view of the user further comprises capturing one or more video images of the field of view of the user.

5. The method of claim 4, wherein the step of displaying the first visual indicator further comprises correlating at least a portion of the one or more video images captured of the individuals participating in the event with at least a portion of the one or more video images captured of the field of view of the user.

6. The method of claim 1, wherein the step of identifying the location of the individual who is currently speaking during the event further comprises:
    capturing audio data of the one or more individuals participating in the event;
    analyzing the audio data to determine which individual is uttering sound indicative of speech;
    designating the individual uttering sound that is indicative of speech as the current speaker; and
    determining the location of the individual designated as the current speaker.

7. The method of claim 6, wherein the step of determining whether the individual identified as the current speaker is within the field of view of the user further comprises capturing directional data associated with the display system and positional data associated with the user.

8. The method of claim 7, wherein the step of displaying the first visual indicator further comprises correlating the location of the current speaker with the directional data associated with the display system and the positional data associated with the user.

9. The method of claim 1, wherein the first visual indicator comprises a marker displayed in proximity to a representation of the individual identified as the current speaker on the display system.

10. The method of claim 1, wherein the first visual indicator comprises a change in at least one attribute associated with a representation of the individual identified as the current speaker on the display system.

11. The method of claim 10, wherein the attribute is one of color and brightness.

12. The method of claim 1, further comprising the steps of:
    obtaining a textual transcription of audio content associated with the event as provided by the one or more individuals; and
    displaying the textual transcription of the audio content to the user in accordance with the display system.

13. The method of claim 12, wherein the step of obtaining the textual transcription comprises at least one of human stenography and automatic speech recognition.

14. Apparatus for providing a user with one or more visual indications of who is currently speaking during an event in which the user is engaged, the event including one or more other individuals, the apparatus comprising:
at least one processing device operative to, in accordance with data captured in association with the event: (i) identify the location of the individual who is currently speaking during the event; and (ii) determine whether the individual identified as the current speaker is within a field of view of the user; and
a display, coupled to the at least one processing device, and operative to: (i) display a first visual indicator to the user in association with the individual identified as the current speaker when the individual is within the field of view of the user; and (ii) display a second visual indicator to the user when the individual identified as the current speaker is not within the field of view of the user, wherein the second visual indicator comprises a directional symbol displayed on the display indicating to the user the direction to turn such that the current speaker is in the user's field of view.

15. The apparatus of claim 14, wherein the at least one processing device and the display are worn by the user.

16. The apparatus of claim 15, wherein the display is a head mounted display.

17. The apparatus of claim 14, wherein the first visual indicator comprises a marker displayed in proximity to a representation of the individual identified as the current speaker on the display.

18. The apparatus of claim 14, wherein the first visual indicator comprises a change in at least one attribute associated with a representation of the individual identified as the current speaker on the display.

19. The apparatus of claim 18, wherein the attribute is one of color and brightness.

20. The apparatus of claim 14, wherein the at least one processing device is further operative to obtain a textual transcription of audio content associated with the event as provided by the one or more individuals, and the display is further operative to display the textual transcription of the audio content to the user in accordance with the display system.

21. A system for providing a user with one or more visual indications of who is currently speaking during an event in which the user is engaged, the event including one or more other individuals, the system comprising:
one or more video cameras for capturing video images of the one or more individuals participating in the event;
a video server coupled to the one or more video cameras and operative to: (i) analyze the captured video images to determine which individual has one or more facial features indicative of speech; and (ii) identify the location of the individual who is currently speaking during the event;
a second video camera for capturing video images of a field of view of the user;
a wearable personal computer coupled to the video server and the second video camera and operative to: (i) obtain the location of the individual who is currently speaking during the event from the video server and at least a portion of the video images of the field of view of the user from the second video camera; (ii) determine whether the individual identified as the current speaker is within a field of view of the user; (iii) generate a first visual indicator in association with the individual identified as the current speaker when the individual is within the field of view of the user; and (iv) generate a second visual indicator when the individual identified as the current speaker is not within the field of view of the user; and
a wearable display, coupled to the wearable personal computer, and operative to display the first and second visual indicators to the user.

22. The system of claim 21, wherein the first visual indicator comprises a marker displayed in proximity to a representation of the individual identified as the current speaker on the wearable display.

23. The system of claim 21, wherein the first visual indicator comprises a change in at least one attribute associated with a representation of the individual identified as the current speaker on the wearable display.

24. The system of claim 23, wherein the attribute is one of color and brightness.

25. The system of claim 21, wherein the second visual indicator comprises a directional symbol displayed on the wearable display indicating to the user the direction to turn such that the current speaker is in the user's field of view.

26. The system of claim 21, further comprising a transcription service coupled to the wearable personal computer and operative to obtain a textual transcription of audio content associated with the event as provided by the one or more individuals in accordance with one or more microphones, such that the wearable personal computer causes the display of the textual transcription of the audio content to the user in accordance with the wearable display.

* * * * *